(12) United States Patent
Jahns et al.

(10) Patent No.: US 8,057,387 B2
(45) Date of Patent: Nov. 15, 2011

(54) SYSTEM, METHOD AND APPARATUS FOR REGULATING VACUUM SUPPLIED TO SURGICAL TOOLS

(75) Inventors: Scott E. Jahns, Hudson, WI (US); Glen Holmberg, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 1419 days.

(21) Appl. No.: 11/411,272

(22) Filed: Apr. 26, 2006

(65) Prior Publication Data
US 2008/0009679 A1    Jan. 10, 2008

Related U.S. Application Data

(60) Continuation of application No. 10/925,387, filed on Aug. 25, 2004, now Pat. No. 7,066,882, which is a division of application No. 10/133,010, filed on Apr. 26, 2002, now Pat. No. 6,800,058.

(51) Int. Cl.
*A61B 1/32* (2006.01)
*F16K 31/12* (2006.01)

(52) U.S. Cl. .................. 600/210; 137/487.5; 137/907; 433/95

(58) Field of Classification Search .............. 600/201, 600/210; 137/487.5, 907, 500, 505.13, 505.18, 137/601.13, 601.2; 433/91–96
See application file for complete search history.

(56) References Cited

U.S. PATENT DOCUMENTS

| | | |
|---|---|---|
| 3,675,072 A | 7/1972 | Hahn et al. |
| 4,270,525 A | 6/1981 | Furihata |
| 4,408,598 A | 10/1983 | Ueda |
| 4,469,484 A | 9/1984 | Kurtz et al. |
| 4,592,198 A | 6/1986 | Stahlecker |
| 4,677,820 A | 7/1987 | Stahlecker |
| 4,699,138 A | 10/1987 | Behrstock |
| 4,769,591 A | 9/1988 | Binet et al. |
| 4,830,045 A * | 5/1989 | Fujikawa et al. ............. 137/456 |
| 4,838,281 A | 6/1989 | Rogers et al. |
| 4,889,531 A | 12/1989 | D'Antonio et al. |
| 4,934,399 A | 6/1990 | Cho |
| 4,971,034 A | 11/1990 | Doi et al. |
| 5,003,966 A | 4/1991 | Saka et al. |

(Continued)

FOREIGN PATENT DOCUMENTS
WO    WO 00/10466    3/2000

*Primary Examiner* — Thomas C. Barrett
*Assistant Examiner* — Michael T Schaper

(57) ABSTRACT

A system, method and apparatus for regulating vacuum applied to surgical suction devices allowing the use of a single vacuum regulator and associated canister to provide vacuum to two suction devices, such as a suction stabilizer and a suction retractor. Vacuum controllers may be placed in the vacuum lines provided to each of two or more suction devices, or may be placed only in the vacuum line of the suction device believed most likely to detach during the procedure. Each vacuum controller is provided with a primary vacuum line, coupling its associated suction device to the output of the vacuum regulator and a pilot passage, also coupling the suction device to the vacuum regulator. The controller closes a valve in the main vacuum line in response to loss of vacuum attachment, which valve remains closed until attachment is reestablished. Closure of the valve results in substantial or complete blockage of the main vacuum line. The pilot passage, which may be part of the valve or a separate vacuum line, serves to allow reestablishment of vacuum attachment while the valve is closed. The pilot passage is configured so that airflow through the pilot passage is low enough that the other suction device or devices coupled to the vacuum regulator can still maintain vacuum attachment.

8 Claims, 9 Drawing Sheets

U.S. PATENT DOCUMENTS

| | | |
|---|---|---|
| 5,299,561 A | 4/1994 | Yoshimoto |
| 5,335,655 A | 8/1994 | Kee |
| 5,337,780 A | 8/1994 | Kee |
| 5,377,672 A | 1/1995 | Kee |
| 5,439,022 A | 8/1995 | Summers et al. |
| 5,570,694 A | 11/1996 | Rometsch |
| 5,582,203 A | 12/1996 | Palmer |
| 5,674,226 A | 10/1997 | Doherty et al. |
| 5,720,314 A * | 2/1998 | Palmer .......................... 137/114 |
| 6,070,582 A | 6/2000 | Kee |
| 6,283,937 B1 | 9/2001 | Takamatsu et al. |
| 6,506,149 B2 | 1/2003 | Peng et al. |
| 6,558,314 B1 | 5/2003 | Adelman et al. |
| 6,641,604 B1 | 11/2003 | Adelman et al. |
| 6,837,852 B2 | 1/2005 | Wu et al. |
| 2002/0091300 A1 | 7/2002 | Peng et al. |
| 2005/0049463 A1 | 3/2005 | Arai et al. |

* cited by examiner

SYSTEM, METHOD AND APPARATUS FOR REGULATING VACUUM SUPPLIED TO SURGICAL TOOLS

CROSS REFERENCE TO RELATED APPLICATIONS

This application is a continuation of U.S. patent application Ser. No. 10/925,387, filed Aug. 25, 2004 now U.S. Pat. No. 7,066,882, which is a divisional of U.S. patent application Ser. No. 10/133,010, filed Apr. 26, 2002 now U.S. Pat. No. 6,800,058.

BACKGROUND OF THE INVENTION

The present invention relates generally to surgical instruments and more particularly to surgical instruments that engage body tissue by means of applied vacuum, such as suction stabilizers and suction retractors employed in coronary artery bypass surgery.

In order to avoid the risks and difficulties associated with cardiopulmonary bypass, various procedures for performing coronary artery bypass on the beating heart have been developed. Several of these procedures employ devices which stabilize a desired anastomosis site by means of suction pods placed on either side of the anastomosis site and devices which hold the heart in a desired position by means of a larger suction pod, typically placed on or near the apex of the heart. Devices of the first type are referred to herein as "suction stabilizers". Devices of the second type are referred to herein as "suction retractors". It is common for procedures to be performed using one of each type of device.

In procedures where both a suction stabilizer and a suction retractor are employed, it is conventional to attach each of the devices to a vacuum source through a separate vacuum regulator and associated canister. While both the stabilizer and the retractor could be coupled to a single vacuum regulator, this is not typically done because a loss of vacuum attachment by one device could readily trigger a loss of vacuum attachment by the other device. The consequences of this loss of attachment would be particularly severe in the context of the suction retractor. However, as sudden detachment of either type of device is undesirable, physicians have typically employed separate vacuum regulators, canisters and vacuum lines for each suction device, in spite of the fact that this results in significant additional equipment being present in the operating room and additional complexity in equipment set-up, as compared to the use of a single vacuum regulator.

SUMMARY OF THE INVENTION

The present invention allows the use of a single vacuum regulator and associated canister to provide vacuum to two suction devices, and in particular to provide vacuum to a suction stabilizer and a suction retractor concurrently. The invention accomplishes this result by means a vacuum controller or controllers associated with the suction devices, located in the vacuum line between the vacuum regulator and the suction device. In operation vacuum controllers may be placed in the vacuum lines provided to each of two or more suction devices, or may be placed only in the vacuum line of the suction device believed most likely to detach during the procedure.

Each vacuum controller is provided with a primary vacuum line, coupling its associated suction device to the output of the vacuum regulator and a pilot passage for coupling the suction device to the vacuum regulator. The controller closes a valve in the main vacuum line in response to loss of vacuum attachment, which valve remains closed until attachment is reestablished. Closure of the valve results in substantial or complete blockage of the main vacuum line, depending on the particular form of the invention. The portion of the main vacuum line between the valve and the suction device is referred to herein as the "downstream" portion of the line, while the portion of the main vacuum line between the valve and the vacuum regulator is referred to herein as the "upstream" portion of the line. The pilot passage serves to allow reestablishment of vacuum attachment while the main vacuum line is closed. The pilot passage is configured so that airflow through the pilot passage is low enough that the other suction device or devices coupled to the vacuum regulator can still maintain vacuum attachment.

In a first embodiment of the invention, the controller is provided with a solenoid valve in the main vacuum line, coupled to a vacuum switch that monitors vacuum in the downstream portion of the main vacuum line. The vacuum controller also includes a battery for powering the solenoid valve and may optionally include a voltage indicator, to indicate the condition of the battery. In the event that vacuum attachment of a the device coupled to the controller is lost, the vacuum in the main vacuum line will rapidly drop and the switch will shut the solenoid valve in the main vacuum line, leaving the pilot line open. When the detached suction device is reapplied to the heart's surface, vacuum applied through the pilot passage serves to reestablish vacuum attachment and to reestablish vacuum in the downstream portion of the main suction line. Restoration of vacuum in the main vacuum line in turn triggers the vacuum switch to open the solenoid valve on the main suction line, restoring full vacuum to the reattached device.

A second embodiment of the invention employs a vacuum operated valve in the main vacuum line. The valve is maintained in an open position by the vacuum in the downstream portion of the main vacuum line. When vacuum attachment of the associated suction device is lost, the vacuum operated valve closes the main line. When vacuum is restored in the downstream portion of the main vacuum line due to reattachment of the device, the valve opens the main vacuum line and provides full vacuum to the suction device in a manner analogous to that described above.

In either the first or second embodiment of the invention, the pilot passage may take various forms. In one form, the pilot passage is a separate line, parallel to the main vacuum line, but bypassing the valve in the main vacuum line. In such cases, flow through the pilot line will be limited either by the size of the line itself or by a flow limiter such as a needle valve or other restrictive orifice. In an alternative form, the pilot passage may be associated with the valve. In some cases, the pilot passage may be defined by the valve itself, and may provide for limited flow through the valve while the valve is closed. This desired result can be accomplished, for example, by a separate limited flow passageway moved into position between the upstream and downstream portions of the main vacuum line during valve closure. Alternatively, the valve may simply be configured to allow a defined level of leakage in the closed position. In other cases, the valve may instead switch the connection of the upstream portion of the main vacuum line to a pilot line, in turn coupled to the downstream portion of the vacuum line and to the suction device The vacuum controllers may be compact, relatively simple and inexpensive devices that may either be disposable or reusable. The controllers may be located at any convenient location within the operating room along the length of the vacuum lines to the suction devices.

DETAILED DESCRIPTION OF THE PREFERRED EMBODIMENTS

Figure 1:
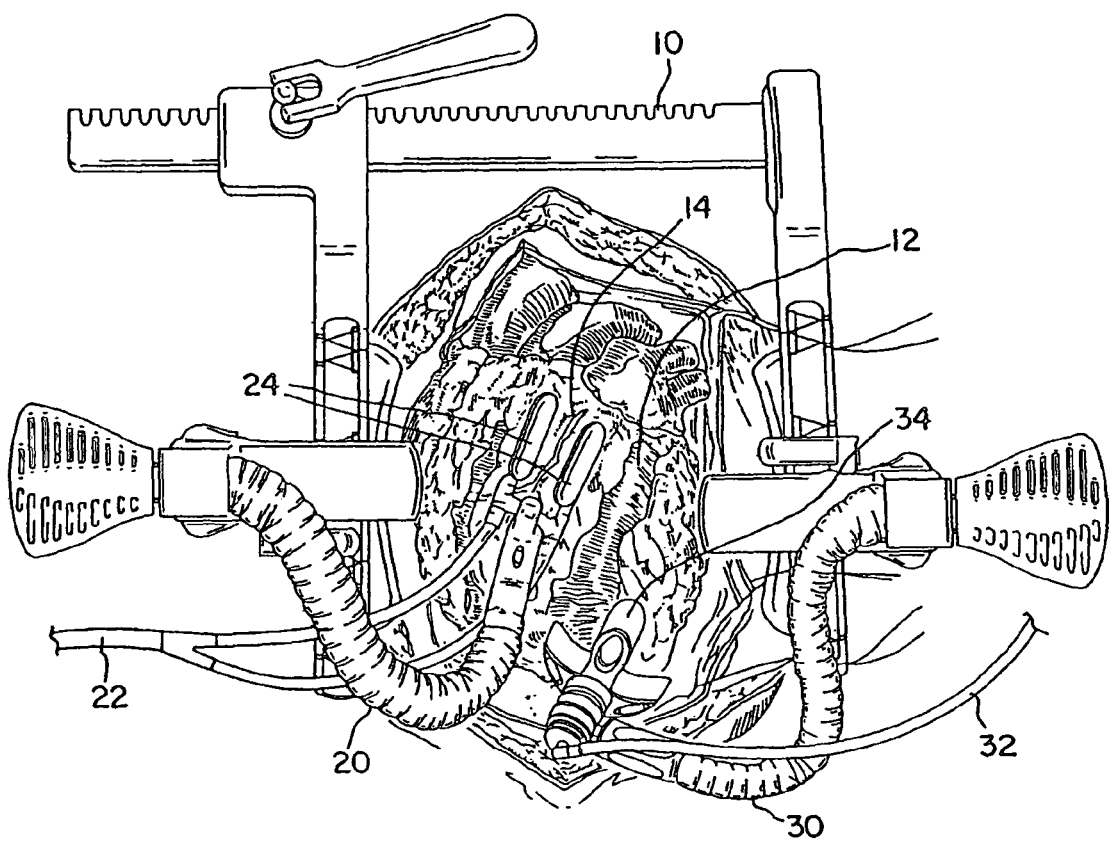
FIG. 1 illustrates a prior art system including a suction stabilizer and a suction retractor mounted to a surgical retractor, showing the stabilizer and the retractor engaging the heart.

FIG. 1 is a perspective view of a surgical system according to the prior art, including a retractor 10 which is employed to spread the patient's ribs providing access to the patient's heart 12, to which a suction retractor 30 and a suction stabilizer 20 have been mounted. The devices as illustrated correspond to the Medtronic Octopus™ Suction Stabilizer and the Medtronic™ Starfish Suction Retractor, as marketed by Medtronic, Inc., Minneapolis, Minn. These devices are commercially available and are generally described in pending U.S. patent application Ser. No. 09/697,294, filed by Keogh, et al. for a "Method and System for Organ Positioning and Stabilization", incorporated herein by reference in its entirety. Each of these devices includes a tissue engagement mechanism, for engaging heart tissue by means of applied vacuum. In the case of the suction stabilizer 20 the tissue engagement mechanism comprises two elongated suction pods 24, each carrying a plurality of suction ports, arranged along their length. As illustrated, the suction pods 24 are placed on either side of a desired anastomosis site on coronary artery 14. The larger suction pod 34 of the suction retractor 30 is applied generally to the apex of the heart, and serves to hold the heart in an elevated, desired position allowing access to coronary artery 14. As illustrated, each of the two devices is provided with a separate suction line 22, 32, which as discussed above, are typically coupled to a separate vacuum regulator and associated collection canister.

Figure 2:
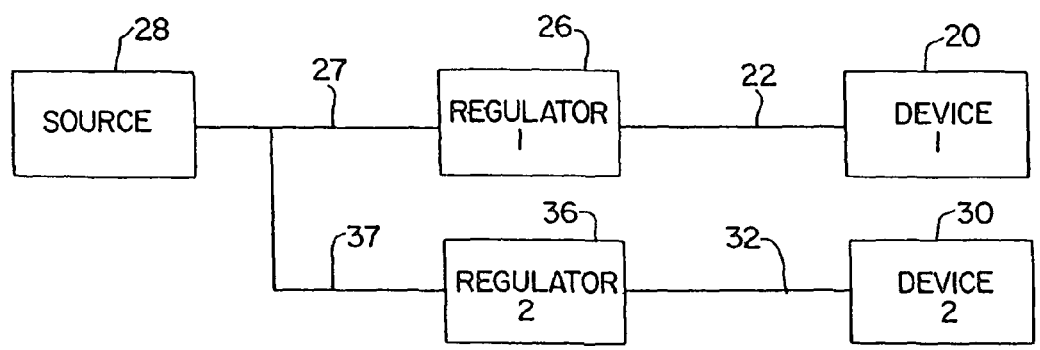
FIG. 2 is a block functional diagram of a prior art system for providing vacuum to the devices illustrated in FIG. 1.

FIG. 2 is a functional block diagram illustrating the provision of vacuum to the suction stabilizer 20 and suction retractor 30 of FIG. 1, according to conventional prior practice. As illustrated, the vacuum lines 22, 32 of each device are coupled to a separate suction regulators 26 and 36, and associated collection canisters (not illustrated). The regulators 26 and 36 are coupled by means of suction lines 27 and 37 to vacuum source 28. This system does require the presence of two regulators and associated suction canisters in the operating room and also requires that the suction lines 22 and 32 of the retractor and stabilizer 20 and 30 must extend from the operative site all the way to the regulators 26 and 36. The requirement of separate vacuum regulators and canisters for each device also results in multiple vacuum tubes being routed through the operating room and requires additional steps in preparing the system.

Figure 3:
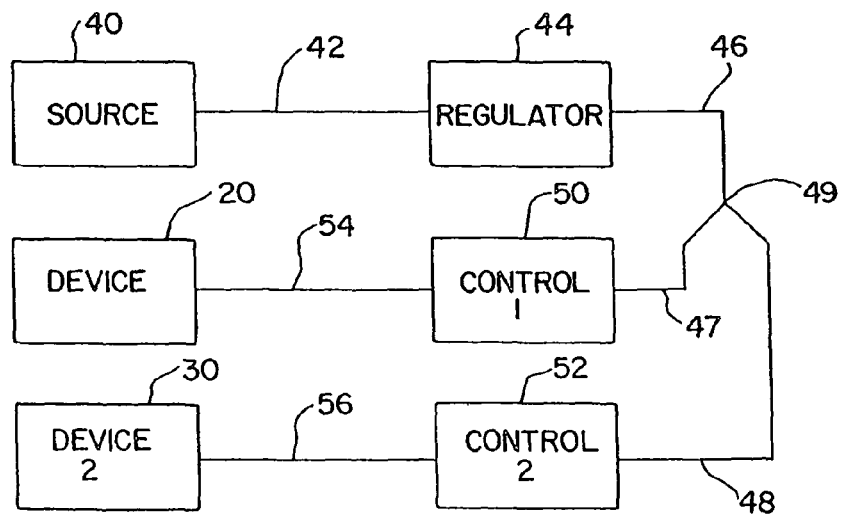
FIG. 3 is a block functional diagram of a system for providing vacuum to two suction devices, according to the present invention.

FIG. 3 is a block functional diagram illustrating the system according to the present invention for providing vacuum to a suction stabilizer 20 and a suction retractor 30 as illustrated in FIG. 1. In this system, vacuum source 40 is coupled to a single vacuum regulator 44 and associated canister by means of a vacuum line 42. The output of the vacuum regulator is coupled by a first suction line 46 to a T or Y fitting 49, which thereafter communicates to vacuum controllers 50 and 52 by means of vacuum lines 47 and 48. Y or T fitting 49 may be located in any convenient location, as may vacuum controllers 50 and 52. Vacuum controller 50 is coupled to the suction stabilizer 20 by means of vacuum line or lines 54 and vacuum control 52 is coupled to the suction stabilizer 30 by means of vacuum line or lines 56, as discussed in more detail below.

Figure 4A:
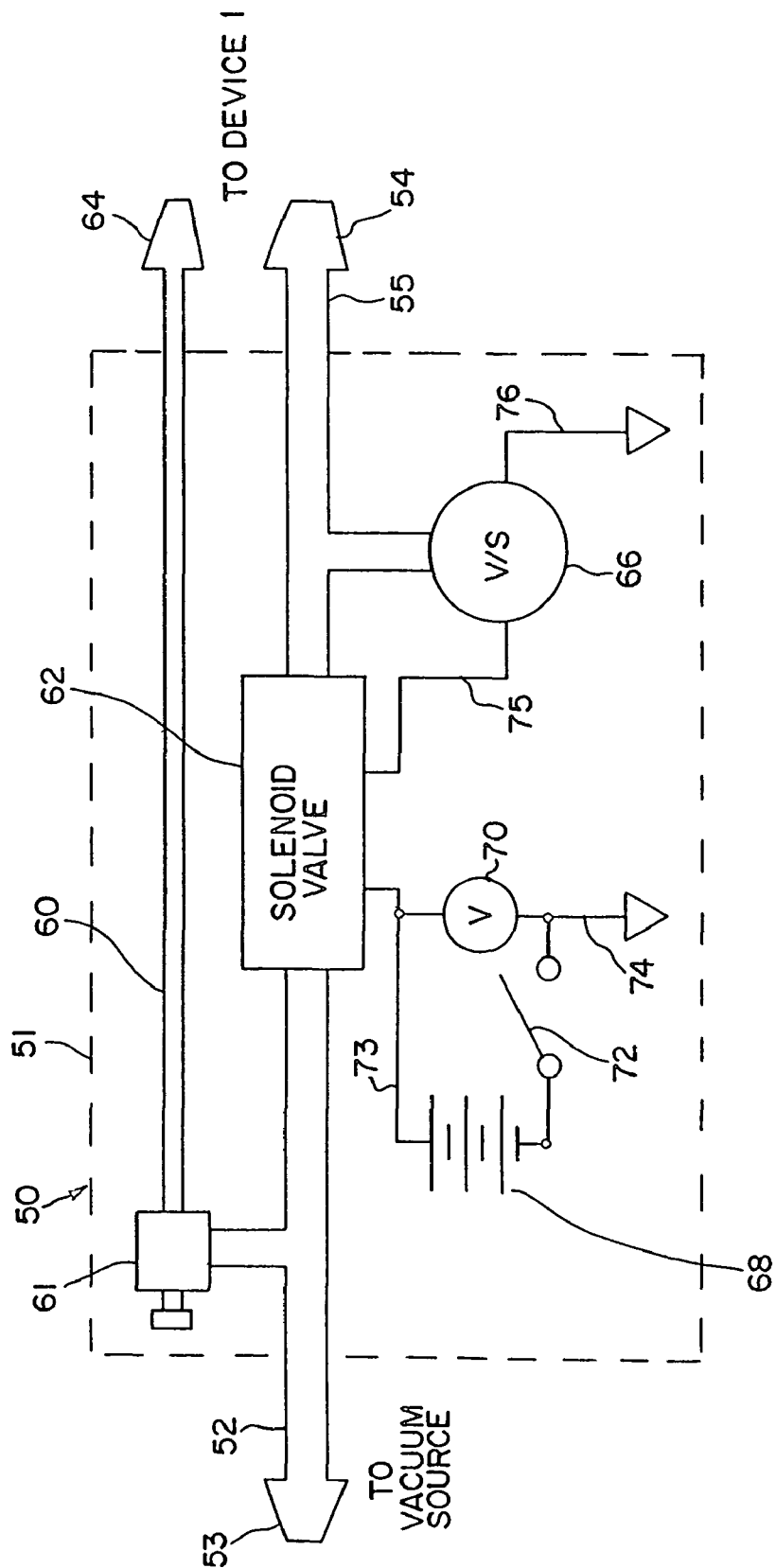
FIG. 4A is a functional schematic drawing illustrating operation of a vacuum controller according to the first embodiment of the present invention.

FIG. 4A is a functional schematic diagram of a suction controller 50, according to the first embodiment of the present invention, in which the pilot passage is located within the solenoid valve. The controller 50 includes a housing, illustrated in broken outline at 51, which contains a solenoid valve 62, a vacuum switch 66, a battery 68, an on/off switch 72 and a voltage monitor 70. The vacuum switch 66 may switch off at approximately 350 mm Hg and switch back on at approximately 50 mm Hg. Appropriate vacuum switches for this and the other designs illustrated in FIGS. 4B and 4C may be obtained, for example, from Air Logic, Inc., Racine, Wis. Appropriate solenoid valves for this and the other designs illustrated in FIGS. 4B and 4C may be obtained, for example, from Mead Fluid Dynamics, Inc., Chicago, Ill. or Pneumadyne, Inc., Plymouth, Minn. In the embodiment illustrated, the housing 50 is provided with a single vacuum input 53 coupled to the upstream portion 52 of the main vacuum line, which in turn is coupled to the input of solenoid valve 62 and to pilot line 60. The output of solenoid valve 62 is coupled to the downstream portion 55 of the main vacuum line and also to an output vacuum coupling 54, which is coupled to a vacuum line extending to the suction device. The pilot line 60 is provided with a separate output vacuum coupling 64, which is to be coupled to the associated suction device by means of an additional vacuum line. An optional voltage monitor 70 and an on/off switch 72 are also provided.

Vacuum switch 66 is coupled to the downstream portion 54 of the main vacuum line, and in response to sensing of a low vacuum due to detachment of an associated suction device, allows electricity to flow from battery 68 through solenoid valve 62 via conductors 73, 74, 75 and 76, to shut the solenoid valve and completely block the main vacuum line. Pilot line 60 remains open, but is configured to allow a relatively limited flow of air, so that the decrease in vacuum at the input 53 of the main vacuum line is relatively minimal. For example, in the context of suction devices intended to operate at about 400 millimeters of mercury vacuum the pilot line 60 may be sized or provided with a flow restrictor such as needle valve 61 which results in a drop of only 50 millimeters of mercury at the vacuum input 53 after closure of the solenoid valve 62.

Vacuum switch 66 in such a system might be configured to close in response to a sensed vacuum of 1-49 millimeters of mercury.

On detachment of the suction device to which the controller 50 is coupled, vacuum in the main vacuum line will fall rapidly, triggering vacuum switch 66 to close solenoid valve 62. Vacuum switch 66 will stay closed until reattachment of the suction device and corresponding restoration of a vacuum greater than 50 millimeters of mercury in the downstream portion 55 of the main suction line. This in turn will open solenoid valve 62, coupling the suction device to the main vacuum line.

As illustrated, the pilot line 60 is provided with a separate vacuum coupling 64 so that the pilot line can be extended to the suction device by means of an additional vacuum line. However, in some cases, the pilot line instead may simply be coupled to the downstream portion 55 of the main vacuum line. In such cases, only a single vacuum line would couple the controller to the suction device. In addition, in the device as illustrated, the vacuum switch 66 is located within the housing 51 of the controller. However, in some cases it may be preferable to locate the vacuum switch on the suction device itself. In such embodiments, conductors 75 and 76 would extend along the vacuum line or lines extending between the suction device and the controller housing.

Figure 4B:
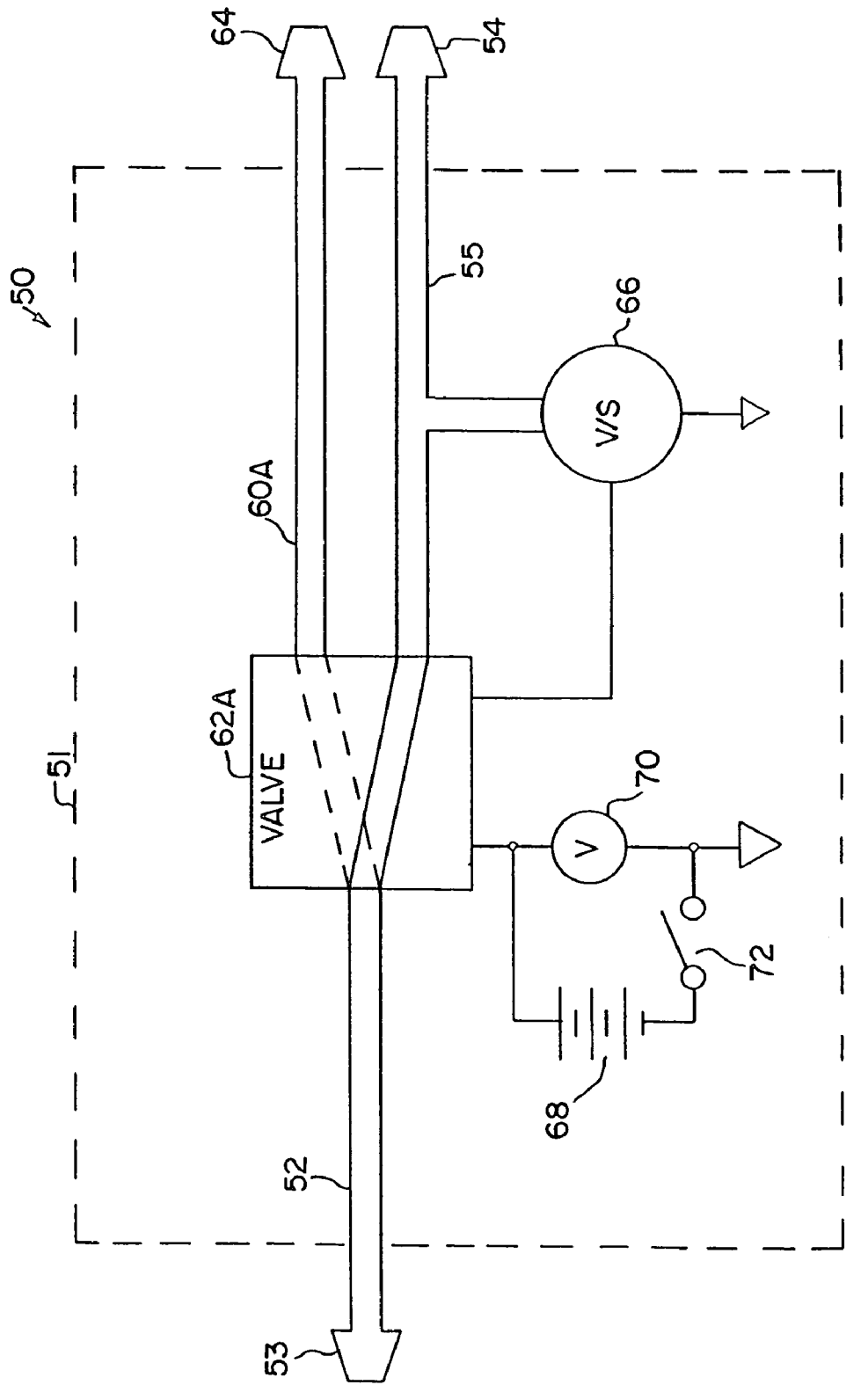
FIG. 4B is a functional schematic drawing illustrating operation of a vacuum controller according to an alternative form of the first embodiment of the present invention.

FIG. 4B is a functional schematic diagram of a suction controller 50, according to an alternative form of the first embodiment of the present invention. Numbered components correspond to identically numbered components in FIG. 4A. In this form of the invention, valve 62A switches the connection of the upstream portion 52 of the main line from to downstream portion 55 of the line to the pilot line 60A, in response to low vacuum in the downstream portion 55 of the main vacuum line sensed by vacuum switch 66. Flow through pilot line pilot line 60A may be simply restricted by its size or by means of a flow restrictor. The flow restrictor may be a part of the valve 62, for example taking the form of a restricted passage within the valve, coupling the upstream portion 52 of the main vacuum line to pilot line 60A.

Figure 4C:
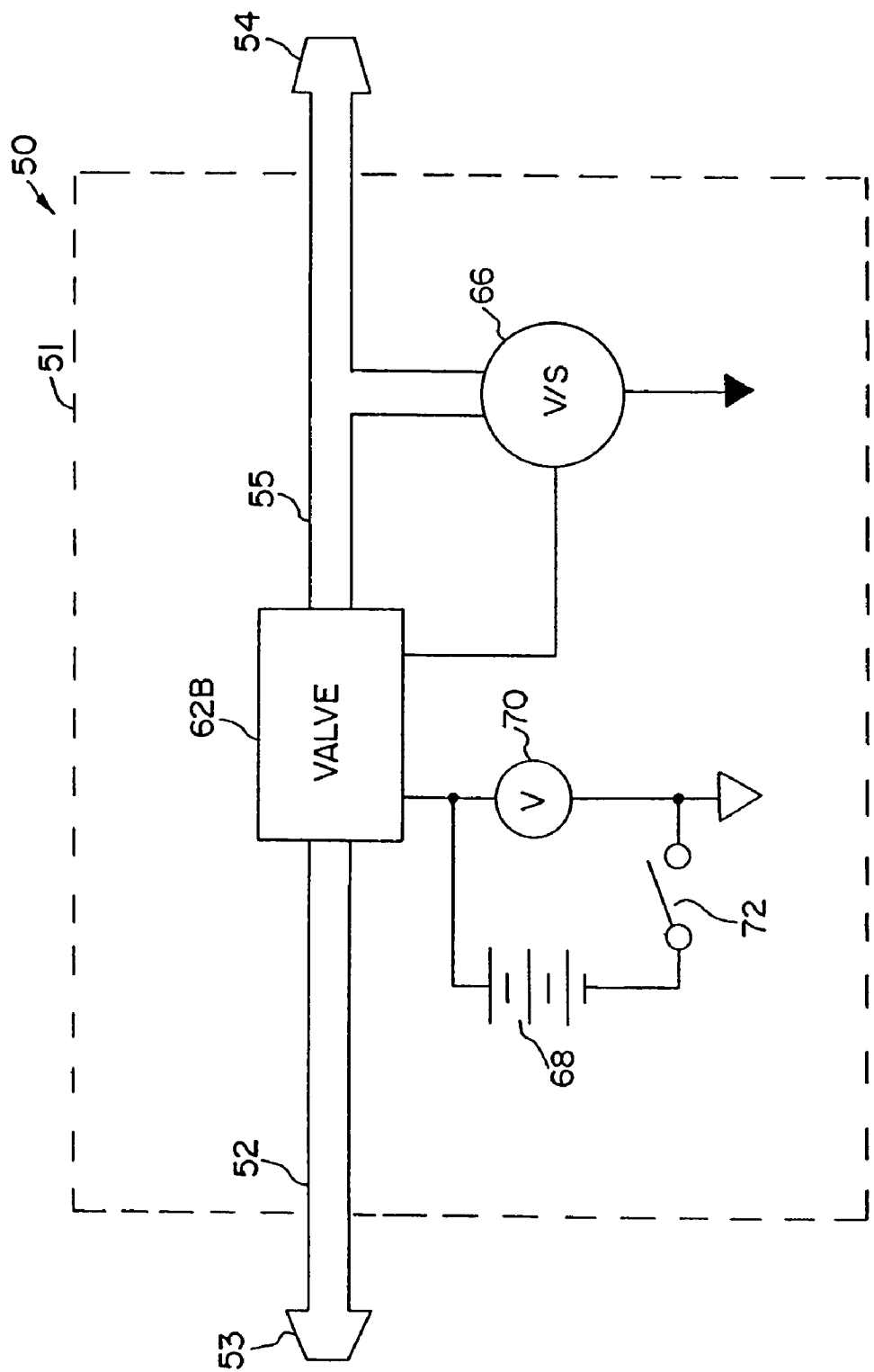
FIG. 4C is a functional schematic drawing illustrating operation of a vacuum controller according to an additional alternative form of the second embodiment of the present invention.

FIG. 4C is a functional schematic diagram of a suction controller 50, according to an additional alternative form of the first embodiment of the present invention. Numbered components correspond to identically numbered components in FIG. 4A. In this form of the invention, Valve 62B incompletely closes the main vacuum line in response to low vacuum detected in the downstream portion 55 of the main vacuum line. The pilot passage in this form of the invention can be a restricted passage through an internal valving member in valve in closed position or can simply be a leakage path through the valve when in the closed position. The leakage path may take the form of a defined passageway not sealed by an internal valving member or may be defined by leakage around an internal valving member which does not completely seat to seal a valve orifice.

Figure 5A:
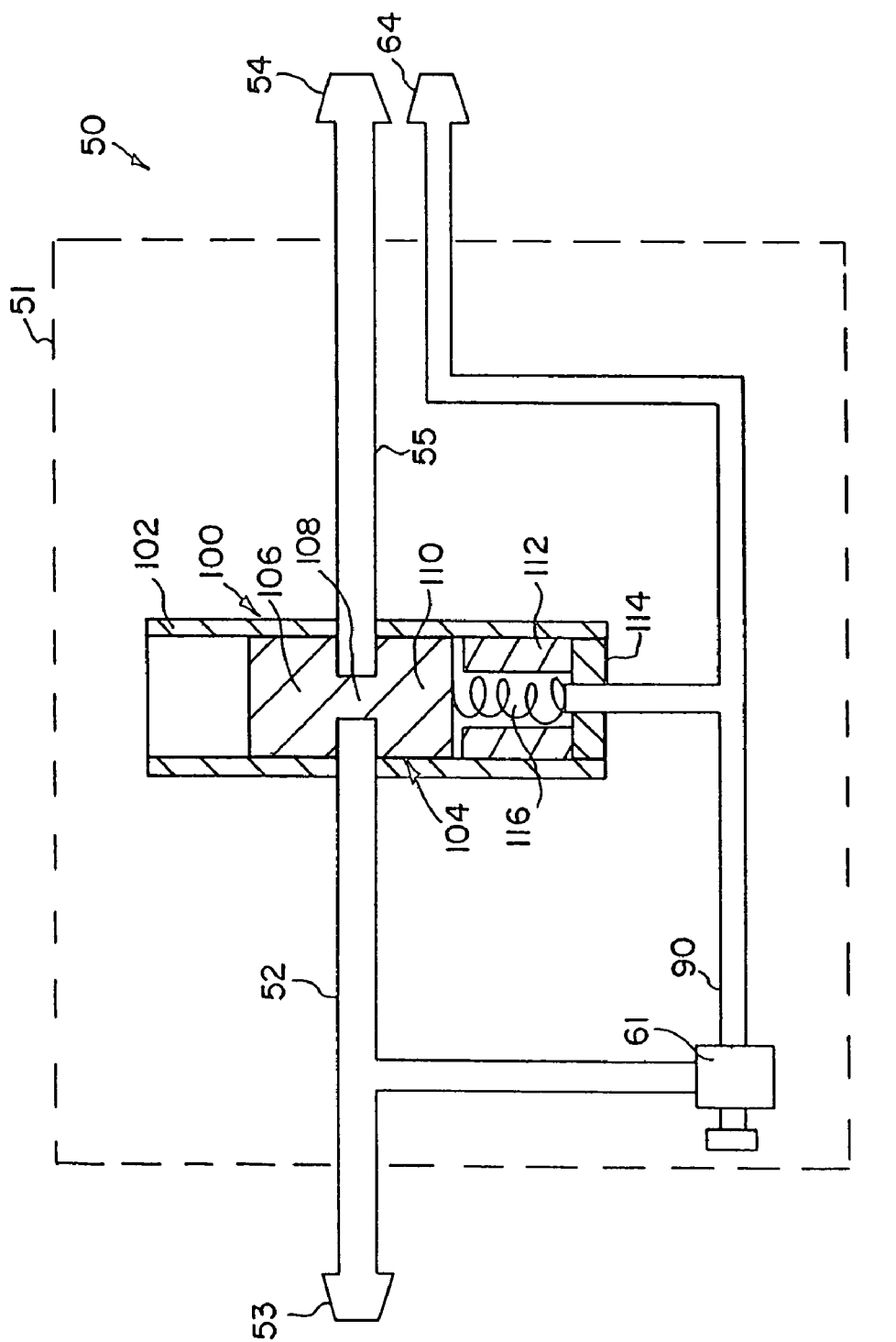
FIG. 5A is a functional schematic drawing illustrating operation of a vacuum controller according to the second embodiment of the present invention.

FIG. 5A is a functional schematic diagram of a suction controller 50, according to the second embodiment of the present invention. Numbered components correspond to identically numbered components in FIGS. 4A-4C, described above. In the embodiment of FIG. 5A, a vacuum operated valve 100 takes the place of the solenoid valves illustrated in FIGS. 4A-4C, discussed above. The vacuum operated valve 100 may structurally resemble an air-dash pot, similar to those manufactured by Airpot Corporation of Norwalk, Conn., but modified to function as a valve. The valve as illustrated includes a tubular housing 102 which may be fabricated, for example of glass and a vacuum piston 104 which may be fabricated, for example of graphite, to assure easy movement of the piston within the tubular housing. The tubular housing 102 includes an inlet port coupled to the upstream portion 52 of the main vacuum line and an outlet port coupled to the downstream portion 55 of the main vacuum line. The piston 104 includes an upper cylindrical section 106, a lower cylindrical section 110 and a center cylindrical section 108 of substantially reduced diameter. A sealing member 114 seals the base of tubular housing 102, and a compression spring 116 is located within tubular spring retainer 112. The upper surface of the spring retainer 112 defines the point of furthest downward movement of the piston 104. Piston 104 is pulled downward against compression spring 116 by means of vacuum applied by means of pilot line 90.

In use, the main vacuum line and the pilot line are coupled to an associated suction device by means of vacuum connectors 54 and 64. When the suction device is attached to tissue, the vacuum level in pilot line 90 is equal to the vacuum level in the main vacuum line, pulling piston 104 downward so that its reduced diameter center portion 110 is aligned with the inlet and outlet ports coupled to the main vacuum line. In this position, full vacuum is applied to the associated suction device. If the associated suction device should suffer detachment, the vacuum level in the pilot line 90 would fall substantially, allowing spring 116 to urge the piston upward so that the lower cylindrical portion 108 of the piston blocks the inlet and outlet ports coupled to the main vacuum line, disconnecting the upstream portion 52 of the main vacuum line from the associated suction device. Spring 116 is preferably chosen to provide a rapid closing of the valve, e.g. closure in one second or less. As discussed in conjunction with the above-described embodiments, vacuum available to the suction device via pilot line 90 is sufficient to allow vacuum reattachment of the device. Upon reattachment of the device, the vacuum levels in pilot line 90 and the downstream portion 55 of the main vacuum line rise to equal that in the upstream portion 52, pulling piston 104 downward and reestablishing connection of the upstream portion 52 of the main vacuum line with the suction device to provide full vacuum. Needle valve 61 may be adjusted to control the time necessary to reestablish a sufficient level of vacuum to open valve 100. While rapid closure of the valve 100 is desirable in order to maintain vacuum at the other suction devices, a more gradual reestablishment of vacuum attachment, e.g. about five seconds, allows the physician to more easily re-position the detached suction device.

Figure 5B:
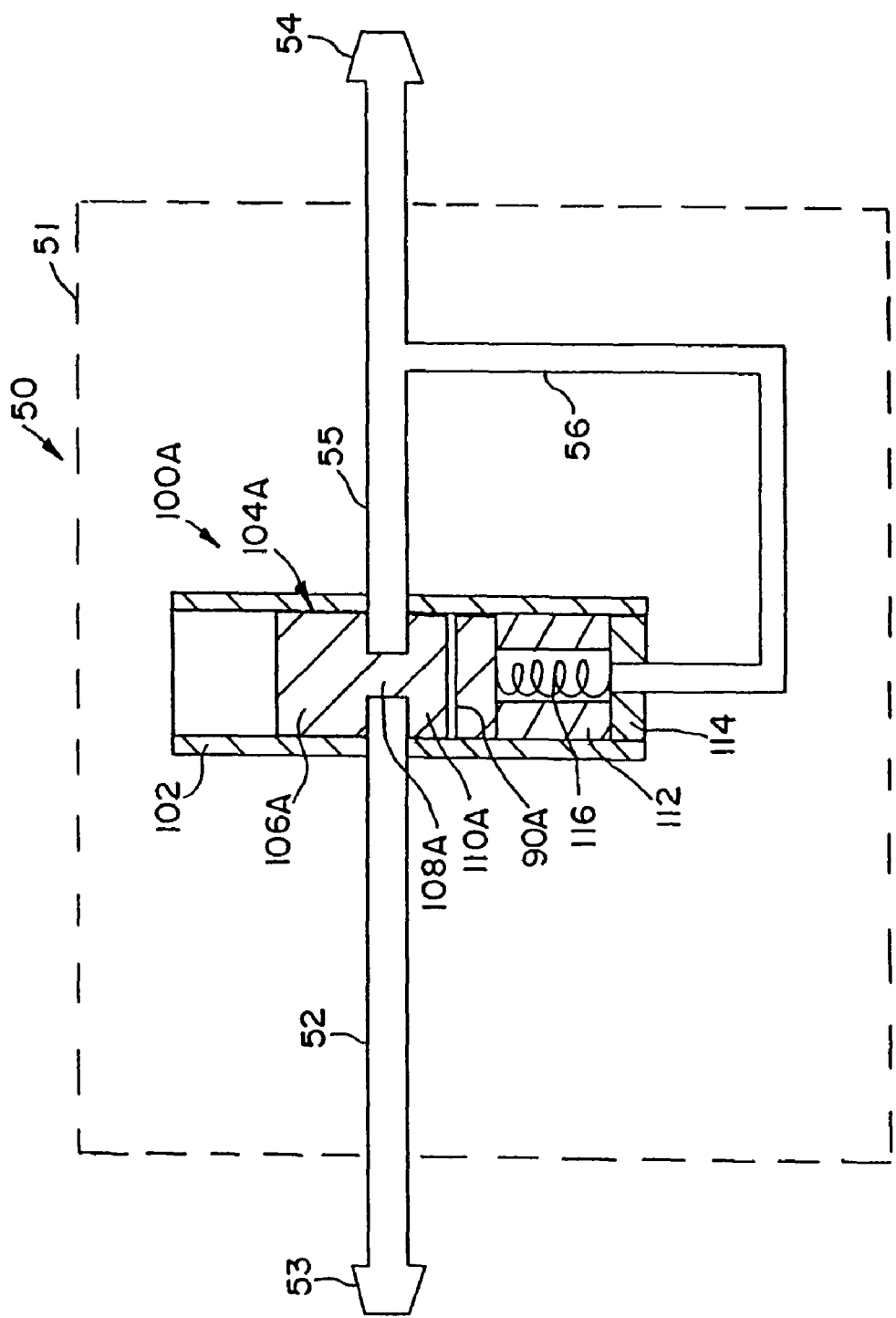
FIG. 5B is a functional schematic drawing illustrating operation of a vacuum controller according to an alternative form of the second embodiment of the present invention.

FIG. 5B is an alternative form of the second embodiment of the present invention. Numbered components correspond to identically numbered components in FIG. 5A above. In this form of the invention, however, the pilot passage 90A takes the form of a narrow bore through the lower cylindrical portion 108A of piston 104A. When vacuum outlet coupling 54 is coupled to an associated vacuum device and vacuum attachment is accomplished, the vacuum in the downstream portion 55 of the main vacuum line is applied to the valve by means of passageway 56, pulling the piston 104A downward against spring 116 so that the narrowed center portion 110A of the piston is aligned with the inlet and outlet ports coupled to the main vacuum line, in the same manner as described above in conjunction with FIG. 5A. On loss of vacuum attachment, vacuum in the downstream portion 55 of the main vacuum line drops rapidly, allowing piston 104A to be moved upward by spring 116, bringing pilot passage 90A into alignment with the inlet and outlet ports of the valve 100A. Like the pilot lines in the embodiments discussed above, pilot passage 90A allows for limited leakage through the valve so that when the associated suction device is reapplied to tissue, vacuum attachment is reestablished via pilot passage 90A, thereafter reestablishing vacuum in line 56, pulling piston 104A downward and restoring full vacuum attachment in the fashion described above in conjunction with FIG. 5A. Preferably, piston 104A is prevented from rotation relative to tubular housing 102, for example by preventing relative rotation of the spring 116, sealing member 114 and piston 104A, by fixed attachment of these components to one another or otherwise.

Figure 5C:
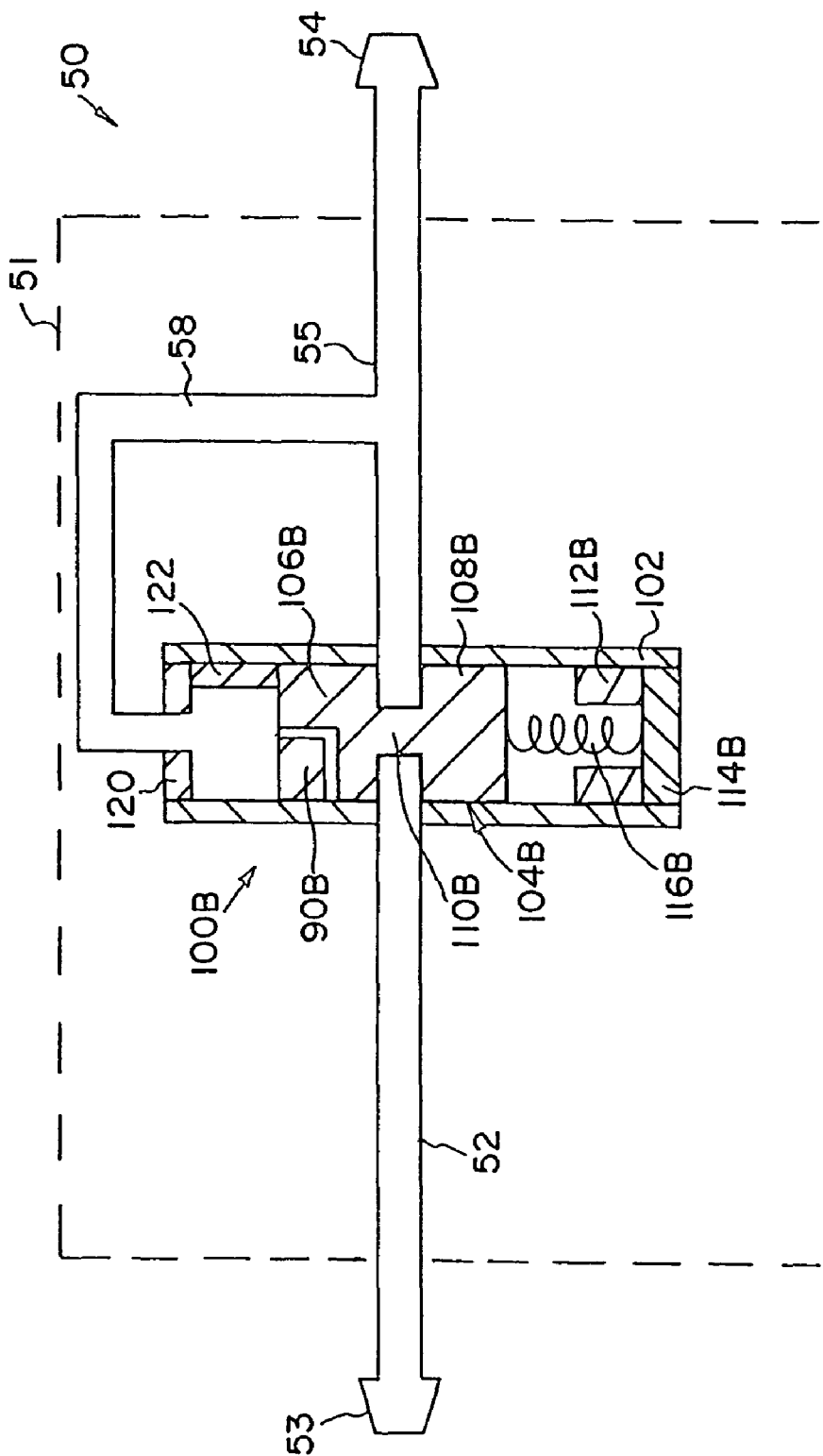
FIG. 5C is a functional schematic drawing illustrating operation of a vacuum controller according to an additional alternative form of the second embodiment of the present invention.

FIG. 5C is a functional schematic diagram illustrating an additional alternative form of the second embodiment of the present invention. All numbered components correspond to identically numbered components in FIGS. 5A and 5B, above. In this form of the invention, the vacuum operated valve 100B employs a tension spring 116B, coupled to the piston 104B and the base seal 114B of the device, tending to pull piston 104B downward. In this version of the invention, vacuum is applied through an upper seal 120 at the top of tubular housing 102 via vacuum passageway 58 coupled to the downstream portion 55 of the main vacuum line. When output coupling 54 is coupled to an associated suction device, vacuum applied to the valve 100B via vacuum passage 58 pulls piston 104B upward until the upper surface of the upper cylindrical portion 106 of the piston lies against piston stop 122. In this position, the reduced diameter center portion 108B of the piston is located aligned with the inlet and outlet ports of tube 102, coupled to the main vacuum line.

On loss of vacuum attachment by the associated suction device, the vacuum level in the downstream portion 55 of the main vacuum line drops rapidly, allowing tension spring 116B to pull piston 104B downward until its lower surface abuts the upper surface of tubular spring retainer 112B. In this position, pilot passage 90B, formed in the upper cylindrical portion 106B of piston 104B is aligned with the upstream portion 52 of the main vacuum line. When the associated suction device is reapplied to tissue, vacuum is provided to the device via pilot passageway 90B, through vacuum passageway 58, allowing for reestablishment of vacuum attachment at the device, in turn allowing vacuum in the downstream portion 55 of the main vacuum line to increase, pulling piston 104B upward against tension spring 116B and realigning the narrowed center portion 110B of the piston with the inlet and outlet ports in the tube and reestablishing full vacuum to the associated suction device. As in the embodiment of FIG. 5B, relative rotation of the piston 104B and tubular housing 102 should be prevented.

While the pilot passage 90D is illustrated in FIG. 5C takes the form of an "L" shaped passageway, in alternative embodiments it might be replaced by a simple groove formed along the outside surface of the upper cylindrical portion 106B of the piston, the groove extending from the upper surface of the piston and terminating above the reduced diameter center portion 110B of the piston. In this form of the invention, fabrication of the pilot passageway 90B is substantially simplified.

Figure 6:
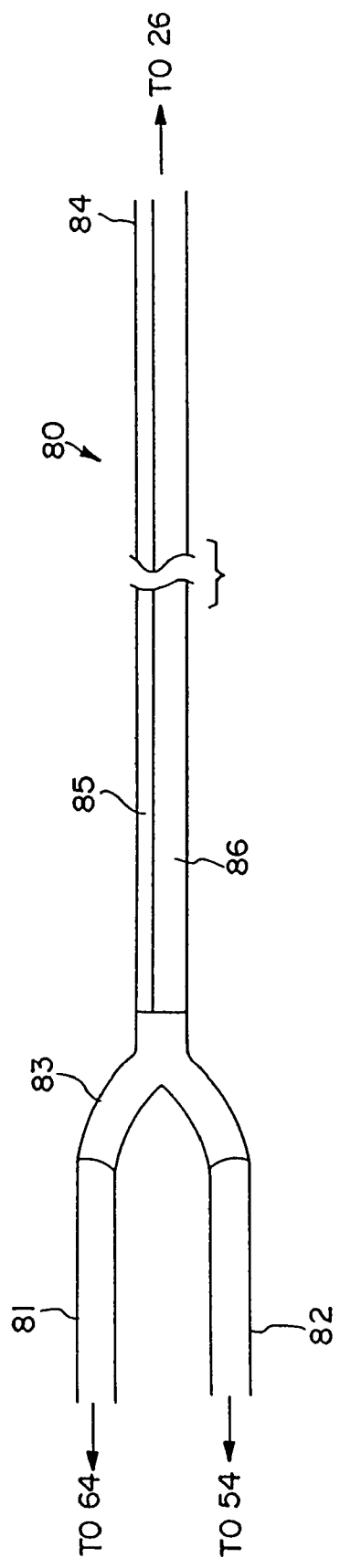
FIG. 6 illustrates a vacuum line set for coupling the controller of FIG. 4A to an associated suction device.

FIG. 6 is an illustration of a composite suction tube intended to attach the controllers FIGS. 4A-4C and 5A to a suction device 20, as in FIG. 1. The tubing 80 includes a Y fitting, bifurcating the tube into two input tubes 81 and 82, which are to be coupled to vacuum couplings 64 and 54 (FIGS. 4A-4C, 5A) respectively. Distal to the Y fitting 83, the tube 80 takes the form of a bitumen tube having a first larger lumen defining a main suction lumen 86 and a smaller second lumen defining a pilot lumen 85. The lumen defining pilot line 85 is, in the embodiment illustrated, terminated prior to the distal portion 84 of the tubing, so that the tubing can be coupled to a single vacuum connector at the suction device. As discussed above, in alternative embodiments, e.g. as in FIGS. 5B and 5C, the pilot passage or pilot line might be located entirely within the housing of the vacuum controller, coupled to the downstream portion 55 of the main vacuum line, allowing the use of only a single vacuum line extending from the controller to the suction device.

As noted above, the present invention was conceived for use primarily in the context of a device that employs vacuum to make an attachment to the tissue of a human heart. However, it is envisioned that such devices may have applications in conjunction with surgery along other portions of the body, and that the invention will be of value in these circumstances as well. As noted above, while the illustration of FIG. 3 assumes a vacuum control will be present for each device, it is also believed that the invention may be usefully practiced using a vacuum control on only one or suction device within the system. In addition, it is envisioned that in future systems, additional vacuum devices may be added to the system. In this case, the invention might usefully be practiced with three or more suction devices, with vacuum controllers coupled to some or all of the devices.

The above embodiments illustrate a variety of approaches to accomplishing the desired purpose of the present invention, which is a vacuum control mechanism which will operate without physician intervention to open full vacuum connection to an associated suction device when the suction device is applied to tissue, to maintain full vacuum to the device as long as the device is vacuum attached to the tissue and to prevent leakage from a detached device from causing substantial drops in vacuum to other suction devices coupled to a common vacuum regulator. While a variety of embodiments are disclosed which perform this function, it is believed that additional alternative embodiments to the present invention can certainly be derived, making use of a pilot line or passageway which remains open after closure of the main vacuum line to allow for vacuum reattachment and reestablishment of full vacuum without substantial reduction in vacuum applied to other commonly connected devices. As such, it is believed that the above embodiments should be considered exemplary, rather than limiting, with regard to the following claims.

In conjunction with the above specification, we claim:

1. A vacuum controller for use with a suction device, comprising:
   a main vacuum line having an upstream portion and a downstream portion;
   means for coupling the downstream portion to the suction device;
   means for coupling the upstream portion to a vacuum source;
   a closeable valve in the main vacuum line between the upstream and downstream portions of the main vacuum line;
   means for closing the valve across the main vacuum line in response to a drop in vacuum in the main vacuum line;
   a pilot passage coupled to the upstream portion of the main vacuum line when the valve is closed; and
   means for coupling the pilot passage to the suction device and providing a vacuum connection from the upstream portion to the suction device when the valve closing the main vacuum line is closed.

2. A controller as in claim 1, wherein the valve couples the pilot passage to the upstream portion of the main vacuum line on closure of the valve.

3. A controller as in claim 1 wherein the valve comprises the pilot passage.

4. A controller as in claim 3 wherein the valve couples the pilot passage to the upstream portion of the main vacuum line on closure of the valve.

5. A controller as in claim 1 wherein the pilot passage comprises a leakage path through the valve while closed.

6. A controller as in claim 1 wherein the pilot passage is continuously connected to the upstream portion of the main vacuum line.

7. A controller as in claim 1 wherein the valve is a solenoid valve and wherein the means for closing the valve in response to a drop in vacuum in the main vacuum line comprises a vacuum switch responsive to vacuum in the downstream portion of the main vacuum line, electrically coupled to the solenoid valve.

8. A controller as in claim 1 wherein the valve is a vacuum operated valve and wherein the means for closing the valve in response to a drop in vacuum in the main vacuum line comprises a vacuum operated valve responsive to vacuum in the main vacuum line.

\* \* \* \* \*